(12) United States Patent
He et al.

(10) Patent No.: US 11,415,721 B2
(45) Date of Patent: Aug. 16, 2022

(54) RESISTIVITY MEASUREMENT METHOD, DEVICE AND SYSTEM

(71) Applicants: PetroChina Company Limited, Beijing (CN); Sichuan Kelite Oil and Gas Technology Co. Ltd, Chengdu (CN)

(72) Inventors: Jiahuan He, Beijing (CN); Keming Zhou, Beijing (CN); Li Zeng, Beijing (CN); Yong Duan, Beijing (CN); Nong Li, Beijing (CN); Fusen Xiao, Beijing (CN); Hongbin Chen, Beijing (CN); Huajie Yu, Beijing (CN); Chunyan Zou, Beijing (CN)

(73) Assignees: PetroChina Company Limited, Beijing (CN); Sichuan Kelite Oil and Gas Technology Co. Ltd, Chengdu (CN)

( * ) Notice: Subject to any disclaimer, the term of this patent is extended or adjusted under 35 U.S.C. 154(b) by 567 days.

(21) Appl. No.: 16/428,641

(22) Filed: May 31, 2019

(65) Prior Publication Data

US 2019/0369286 A1 Dec. 5, 2019

(30) Foreign Application Priority Data

Jun. 5, 2018 (CN) .......................... 201810567063

(51) Int. Cl.
*G01V 3/38* (2006.01)
*G01R 27/08* (2006.01)
(Continued)

(52) U.S. Cl.
CPC .............. *G01V 3/38* (2013.01); *G01R 27/08* (2013.01); *G01V 1/306* (2013.01); *G01V 3/08* (2013.01); *G01V 11/002* (2013.01)

(58) Field of Classification Search
None
See application file for complete search history.

(56) References Cited

U.S. PATENT DOCUMENTS 4,734,649 A 3/1988 Barnaby
4,907,448 A * 3/1990 Givens ................. G01N 33/241
324/376
(Continued)

FOREIGN PATENT DOCUMENTS

CN 102519831 A 6/2012
CN 103293381 A 9/2013
(Continued)

OTHER PUBLICATIONS

Zheng, et al., "Study on the frequency dispersion of the complex resistivity in reservoir rocks based on electroseismic coupling," Chinese Journal of Geophysics, vol. 59, No. 6, pp. 2266-2279, Jul. 2016.
(Continued)

*Primary Examiner* — Lina M Cordero
(74) *Attorney, Agent, or Firm* — Hamilton, Brook, Smith & Reynolds, P.C.

(57) ABSTRACT

The present disclosure discloses a resistivity measurement method, device and system. The method comprises: placing a core to be measured into the core holder after a 100% saturated water treatment, and injecting a predetermined confining pressure by the confining pressure pump; turning on the displacement source to carry out a displacement, and at an interval of a predetermined time period, acquiring a current value by the ammeter and a voltage value by the voltmeter; determining a resistivity of the core according to the current value, the voltage value, an arc length of the curved electrode, and a radius and a length of the core. The present disclosure can realize a rock resistivity measurement in a vertical direction under formation conditions for a
(Continued)

plunger-type core, without needing to change the core preparation technology or method.

10 Claims, 11 Drawing Sheets

(51) Int. Cl.
    *G01V 1/30*     (2006.01)
    *G01V 3/08*     (2006.01)
    *G01V 11/00*     (2006.01)

(56) References Cited

U.S. PATENT DOCUMENTS

| | | | | |
|---|---|---|---|---|
| 4,926,128 A * | 5/1990 | Givens | ............... | G01N 33/241 324/376 |
| 5,093,623 A * | 3/1992 | Givens | ............... | G01N 33/24 324/376 |
| 5,105,154 A * | 4/1992 | Givens | ............... | G01N 33/241 324/376 |
| 5,209,104 A * | 5/1993 | Collins | ............... | G01N 33/241 324/376 |
| 7,019,654 B2 * | 3/2006 | Danyluk | ............... | G01N 27/002 340/450.3 |
| 7,221,165 B2 * | 5/2007 | Fleury | ............... | G01N 27/02 324/376 |
| 2015/0103624 A1 | 4/2015 | Thompson et al. | | |

FOREIGN PATENT DOCUMENTS

| | | |
|---|---|---|
| CN | 104181394 A | 12/2014 |
| CN | 104749652 A | 7/2015 |
| CN | 105258793 A | 1/2016 |
| CN | 105973698 A | 9/2016 |
| CN | 106970000 A | 7/2017 |
| CN | 107748291 A | 3/2018 |
| CN | 108051643 A * | 5/2018 |
| CN | 108051643 A | 5/2018 |
| GN | 1461950 A | 12/2003 |
| GN | 102374963 A | 3/2012 |
| GN | 206095886 U | 4/2017 |

OTHER PUBLICATIONS

Chinese Search Report for Chinese Patent Application No. 201810567063.3, titled: "Resistivity Measurement Method, Device and System", dated Feb. 12, 2019 (With English Translation).
GB/T 29172-2012 "Practices for core analysis," 239 pages, 2012 (with English Abstract).
SY/T 5385-2007 "Measurement and calculation methods of rock resistivity parameters in laboratory," 20 pages, 2007 (with English Abstract).
Chinese Search Report for Chinese Patent Application No. 201810567063.3, titled Resistivity Measurement Method, Device and System, dated Jun. 1, 2018 (with English translation).

* cited by examiner

RESISTIVITY MEASUREMENT METHOD, DEVICE AND SYSTEM

RELATED APPLICATION

This application claims priority under 35 U.S.C. § 119 or 365 to Chinese, Application No. 201810567063.3, filed Jun. 5, 2018. The entire teachings of the above application are incorporated herein by reference.

TECHNICAL FIELD

The present disclosure relates to the technical field of oil and gas exploration and development experiments, and particularly to a resistivity measurement method, device and system.

BACKGROUND ART

The formation resistivity is closely related to the lithology, physical properties and oiliness. By studying the difference between the formation resistivities, analyses and profile comparison can be made for the lithology, physical properties, and pore fluid properties. In the indoor experimental environment, it is an important work of the electrical logging to study the resistivity of the saturated saline rock or a part thereof.

The laboratory measurement of the rock resistivity is made mainly with reference to the industry standard SY/T 5385-2007 *Laboratory Measurement and Calculation Method of Rock Resistivity Parameters*. However, based on the core sampling situation, as illustrated in FIG. 1, at present, a plunger-type core 23 with a diameter of 2.5 cm is generally used for the laboratory measurement of the rock resistivity. The core is drilled in a radial direction x of a full-diameter core 21, so the rock resistivity at either end of the tested plunger-type core 23 represents a resistivity in a horizontal direction under formation conditions, while the resistivity of field logging represents a comprehensive resistivity in directions x, y and z under formation conditions. For an anisotropic reservoir, the physical significances of the two resistivities are obviously different.

For an isotropic reservoir, there is no obvious difference between the results of the conventional laboratory rock resistivity test method and the logging interpretation. However, anisotropic reservoirs still exist in the actual production process. As illustrated in FIG. 2, for example, for a reservoir formed by channel sand, the particles P in the reservoir rock will deposit along the ancient water flow direction x, and immeasurable differences also occur between the rock resistivities in different directions due to various forms of the particles P.

For another example, as illustrated in FIG. 3, for a shale reservoir R with developed laminae, the rock resistivity is also anisotropic in different directions. For a shale reservoir with a high water-saturation in direction y perpendicular to the laminae, the shale matrix has a blocking effect on the electricity conduction, and the resistivity is high in direction y; while since the formation water in the laminae is conductive, the resistivity tested in direction x parallel to the laminae is low.

At present, for an anisotropic reservoir under indoor conditions, one way to test the vertical resistivity under formation conditions is to prepare a rock sample into a cuboid, and apply an electric field in three different directions to acquire a rock resistivity. The shortage of this method is that the rock sample preparation is troublesome. Tedious wire cutting will be taken to make a cuboid core with a regular shape, which is a special core sample preparation method having disadvantages of long-time consumption and tedious technology as compared with the method of using a drilling machine to drill plunger-type cores.

SUMMARY OF THE DISCLOSURE

An objective of the present disclosure is to provide a resistivity measurement method, device and system, which can overcome the defects in the prior art and realize a rock resistivity measurement in a vertical direction under formation conditions for a plunger-type core, without needing to change the core preparation technology or method.

The above objective of the present disclosure can be achieved by the following technical solutions:

A resistivity measurement system, comprising:

at least one displacement loop, comprising a displacement source, an inlet valve, a core holder, an outlet valve and a separation recording device connected in sequence;

a confining pressure pump configured to apply a confining pressure to the core holder;

the core holder is configured to dispose a plunger-type core to be measured, a sleeve is disposed between the core and the core holder, two opposite curved electrodes are disposed on the sleeve, an inner surface of the curved electrode is matched with an outer surface of the sleeve, and the curved electrode is provided with an opening for fluid circulation;

a curved electrode circuit, comprising: a power supply and a switch disposed between the two curved electrodes, a voltmeter configured to measure a voltage between the two curved electrodes, and an ammeter configured to measure a current flowing between the two curved electrodes.

In a preferred embodiment, the curved electrode is in the form of a grid, comprising solid and hollow grid cells, the hollow grid cell being an opening for fluid circulation, and a material of the solid grid cell being conductive metal.

In a preferred embodiment, a centering angle of the curved electrode is greater than 0° and less than 180°.

In a preferred embodiment, the centering angle of the curved electrode is 90°.

In a preferred embodiment, the displacement loop comprises a gas displacing water loop and a water displacing oil loop which share the core holder, the gas displacing water loop sequentially comprises a gas source, a pressure regulation mechanism, a first inlet valve, the core holder, a first outlet valve, and a gas-liquid separation metering device;

the water displacing oil loop sequentially comprises a displacement pump, a water source, a second inlet valve, the core holder, a second outlet valve, and an oil-water separation metering device.

A resistivity measurement method based on the resistivity measurement system aforementioned, comprising:

placing a core to be measured into the core holder after a 100% saturated water treatment, and injecting a predetermined confining pressure by the confining pressure pump;

turning on the displacement source to carry out a displacement, and at an interval of a predetermined time period, acquiring a current value by the ammeter and a voltage value by the voltmeter;

determining a resistivity of the core according to the current value, the voltage value, an arc length of the curved electrode, and a radius and a length of the core.

In a preferred embodiment, determining a resistivity of the core according to the current value, the voltage value, an arc length of the curved electrode, and a radius and a length of the core specifically calculates according to a formula:

$$\rho(S_w) = \frac{h\Delta U}{J} \frac{K(k')}{K(k)}$$

wherein $$K(k) = \int_0^1 \frac{dx}{\sqrt{(1-x^2)(1-k^2x^2)}},$$

k=cos α, k'=sin α, $$\alpha = \frac{l}{2r},$$

ΔU denotes a voltage value acquired by the voltmeter, J denotes a current density, $$J = \frac{I}{A}, A = \frac{\pi rh}{2},$$

I denotes a current value read by the ammeter, r denotes a radius of the core, l denotes an arc length of the curved electrode, h denotes a length of the core, and $S_w$ denotes a water saturation degree of the core.

In a preferred embodiment, the resistivity measurement method further comprises: at the interval of the predetermined time period, acquiring an accumulated liquid amount through the separation recording device, and determining a saturation parameter of the core through the accumulated liquid amount and a pore volume of the core.

In a preferred embodiment, determining a saturation parameter of the core through the accumulated liquid amount and a pore volume of the core specifically calculates according to a formula:

$$S = \left(1 - \frac{V(t)}{V_p}\right) \times 100\%$$

wherein V(t) denotes an accumulated liquid amount, which is measured in a displacement experiment, and $V_P$ denotes a saturation parameter of the core, which is a known value.

A resistivity measurement device, comprising: a data acquisition module, a memory and a processor, wherein the data acquisition module is configured to acquire predetermined data, the memory stores a predetermined correspondence relation for determining a resistivity according to the predetermined data acquired by the data acquisition module, and the processor is capable of determining a resistivity of a core based on the predetermined data acquired by the data acquisition module and the predetermined correspondence relation stored in the memory; wherein the predetermined data comprises arc lengths of curved electrodes oppositely disposed on two sides of the core, voltage values at two ends of each curved electrode, current values flowing through the core, and a length of the core;

the predetermined correspondence relation is:

$$\rho(S_w) = \frac{h\Delta U}{J} \frac{K(k')}{K(k)}$$

wherein $$K(k) = \int_0^1 \frac{dx}{\sqrt{(1-x^2)(1-k^2x^2)}},$$

k=cos α, k'=sin α, $$\alpha = \frac{l}{2r},$$

ΔU denotes a voltage value acquired by the voltmeter, J denotes a current density, $$J = \frac{I}{A}, A = \frac{\pi rh}{2},$$

I denotes a current value read by the ammeter, r denotes a radius of the core, l denotes an arc length of the curved electrode, h denotes a length of the core, $S_w$ denotes a water saturation degree of the core.

The present disclosure has the characteristics and advantages that in the provided resistivity measurement method, device and system, two opposite curved electrodes are disposed outside the sleeve in the core holder, and corresponding curved electrode circuit is disposed to acquire a voltage value and a current value for the resistivity calculation; subsequently, the resistivity of the core is determined according to the current value, the voltage value, an arc length of the curved electrode, and a radius and a length of the core. Experiments prove that the resistivity measurement manners provided by the present disclosure can acquire the resistivity of the plunger-type core in a diameter direction, and are particularly suitable for the anisotropic reservoir.

As compared with the prior art, the present disclosure can realize a rock resistivity measurement in a vertical direction under formation conditions for a plunger-type core, without needing to change the core preparation technology or method.

The specific embodiments of the present application are disclosed in detail with reference to the description and drawings described later, which indicate the manners in which the principle of the present disclosure may be adopted. It should be understood that the scope of the embodiments of the present disclosure is not limited thereto. Within the scope of the spirit and clauses of the appended claims, the embodiments of the present disclosure include many changes, modifications and equivalents.

Features described and/or illustrated for one embodiment may be used in the same or similar manner in one or more other embodiments, combined with the features in other embodiments, or substitute for the features in other embodiments.

It should be emphasized that the term 'comprise/include' used herein refers to the presence of features, integers, steps or components, but does not preclude the presence or addition of one or more other features, integers, steps or components.

DETAILED DESCRIPTION OF THE PREFERRED EMBODIMENTS

The technical solutions of the present disclosure will be described in detail below with reference to the drawings and the specific embodiments. It should be understood that those embodiments are only used to illustrate the present disclosure, rather than limiting the scope thereof. After reading the present disclosure, a person skilled in the art can make various equivalent modifications to the present disclosure, which should fall within the scope defined by the appended claims of the present disclosure.

Unless otherwise defined, any technical or scientific term used herein has the same meaning as that commonly understood by a person skilled in the technical field of the present disclosure. The terms used in the Specification are only for the purpose of describing the specific embodiments and not intended to limit the present disclosure.

It should be noted that when an element is referred to as being 'disposed on' another element, it may be directly on another element or there may be an intermediate element. When an element is deemed as being 'connected to' another element, it may be directly connected to another element or there may be an intermediate element at the same time. The terms 'vertical', 'horizontal', 'upper', 'lower', 'left', 'right' and the like used herein are for illustration purposes only, rather than indicating a unique embodiment.

The present disclosure provides a resistivity measurement method, device and system, which can overcome the defects in the prior art and realize a rock resistivity measurement in a vertical direction under formation conditions for a plunger-type core, without needing to change the core preparation technology or method.

Figure 1:
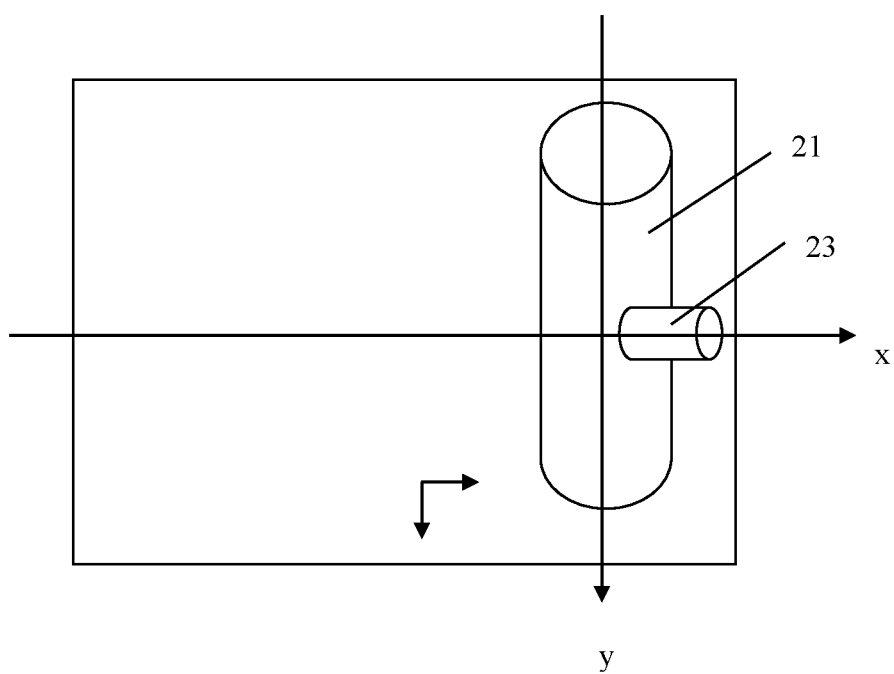
FIG. 1 illustrates a directional diagram of a laboratory measurement of a rock resistivity.
Figure 2:
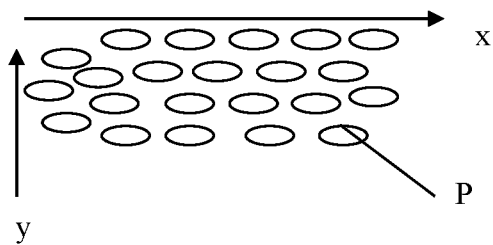
FIG. 2 illustrates a principle diagram of anisotropy of a rock resistivity in different directions of channel sandstone.
Figure 3:
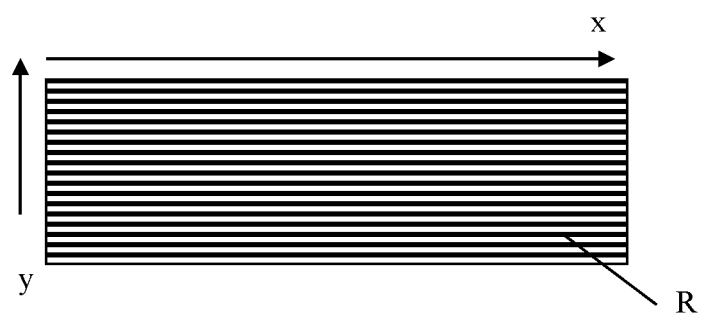
FIG. 3 illustrates a principle diagram of anisotropy of a rock resistivity in different directions of a shale reservoir with developed laminae.
Figure 4:
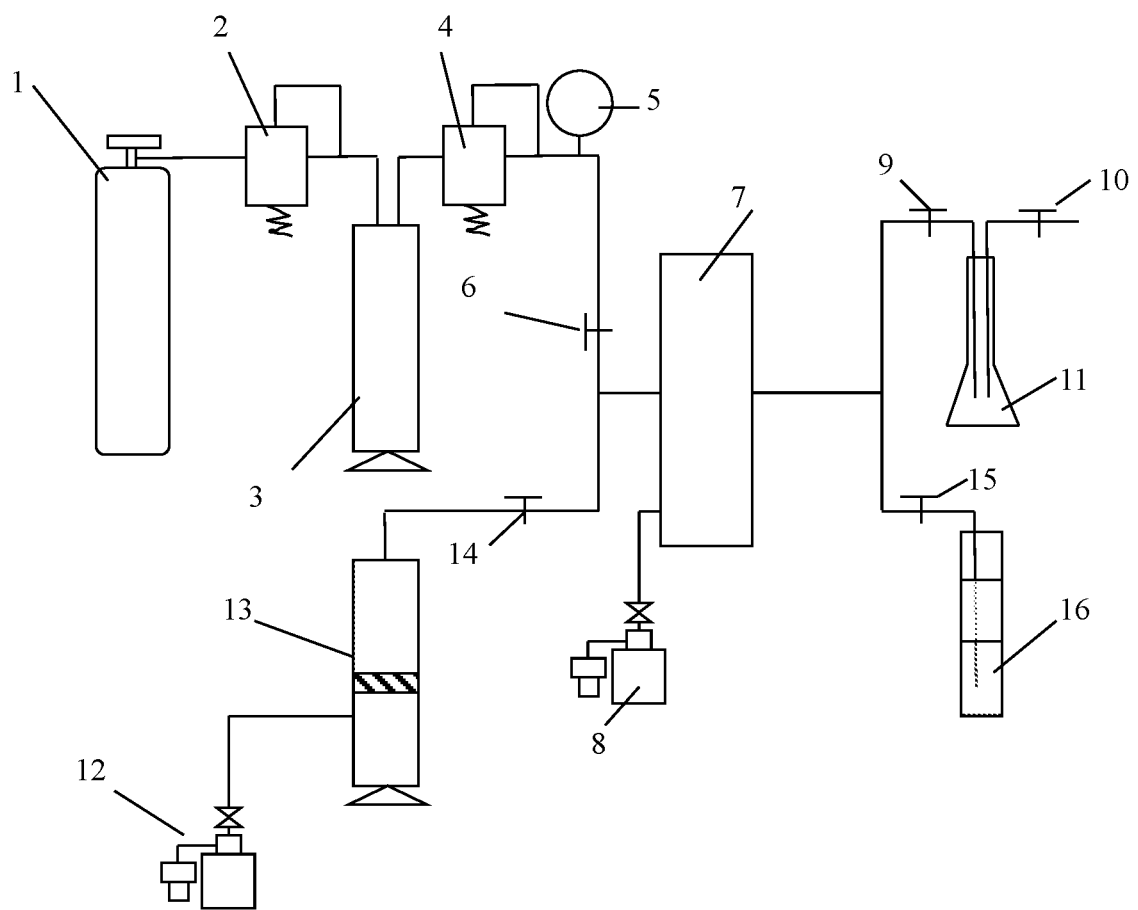
FIG. 4 illustrates a structural diagram of a resistivity measurement system provided in an embodiment of the present disclosure.
Figure 5:
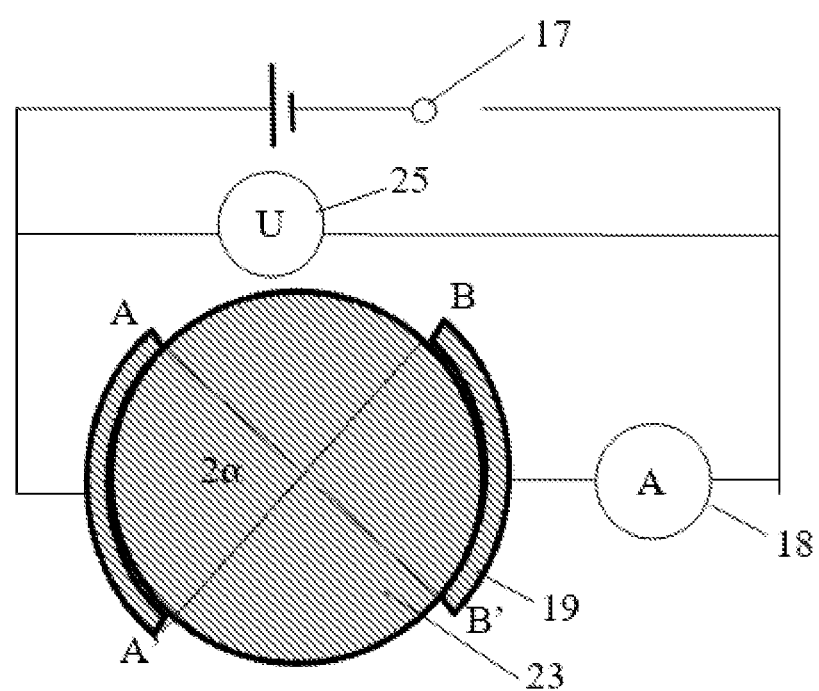
FIG. 5 illustrates a schematic diagram of a curved electrode circuit provided in an embodiment of the present disclosure.

Referring to FIGS. 4 and 5, which illustrate a resistivity measurement system provided in an embodiment of the present application, comprising: at least one displacement loop comprising a displacement source, an inlet valve, a core holder 7, an outlet valve and a separation recording device connected in sequence; a confining pressure pump 8 configured to apply a confining pressure to the core holder 7; the core holder 7 is configured to dispose a plunger-type core to be measured, a sleeve is disposed between the core and the core holder 7, two opposite curved electrodes 19 are disposed on the sleeve, an inner surface of the curved electrode 19 is matched with an outer surface of the sleeve, and the curved electrode 19 is provided with an opening for fluid circulation; and a curved electrode circuit comprising: a power supply and a switch 17 disposed between the two curved electrodes 19, a voltmeter 25 configured to measure a voltage between the two curved electrodes 19, and an ammeter 18 configured to measure a current flowing between the two curved electrodes 19.

In this embodiment, the kernel of the resistivity measurement system is the core holder 7 provided with the curved electrodes 19. The core holder 7 is contacted with the core through a rubber sleeve having two special curved surfaces. The two curved surfaces have two functions, i.e., one is to act as the curved electrodes 19 and mainly used for resistivity measurement, and the other is to act as a fluid inlet and a fluid outlet during seepage.

In this embodiment, the curved electrode 19 has opposite inner and outer surfaces, wherein the inner surface of the curved electrode 19 is bonded to the surface of the core with a rubber sleeve spacing therebetween. The shape and size of the inner surface of the curved electrode 19 are matched with those of the surface of the core.

In which, the schematic diagram of the curved electrode circuit disposed for the core holder 7 provided with the curved electrodes 19 is illustrated in FIG. 5. The curved electrode circuit comprises: a power supply and a switch 17 disposed between the two curved electrodes 19, a voltmeter 25 configured to measure a voltage between the two curved electrodes 19, and an ammeter 18 configured to measure a current flowing between the two curved electrodes 19.

As illustrated in FIG. 5, the centering angles corresponding to the surfaces of the curved electrodes 19 are all 2a, wherein the value of 2a is greater than 0 and less than 180, thereby ensuring that a certain gap is formed between the end faces of the two opposite curved electrodes 19 and no direct conduction will occur. In order to simplify the calculation, the value of 2a may be 90 degrees.

The curved electrode 19 specifically may be in the form of a grid, and it may comprise solid and hollow grid cells, wherein the hollow grid cell is an opening for fluid circulation, and a material of the solid grid cell is conductive metal. Specifically, a plane development diagram of the curved electrode 19 is illustrated in FIG. 6a or 6b, wherein the shaded solid grid cells represent metal, which usually may be copper or silver with good conductivity; and the hollow grid cells without shadow represent the blanks, i.e. the channels for fluid inflow and outflow.

Figure 6A:
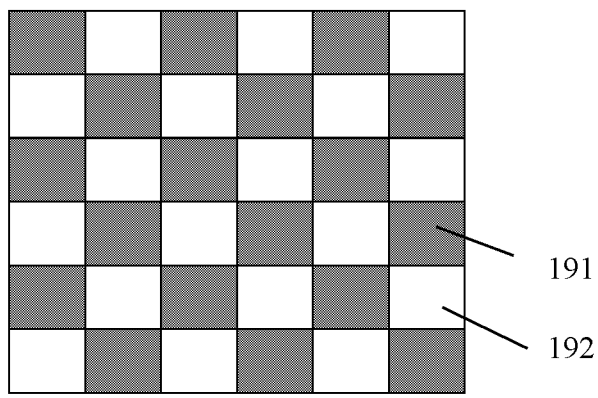
FIG. 6a illustrates a plane development diagram of a curved electrode provided in an embodiment of the present disclosure.

Specifically, FIG. 6a illustrates a ½ type curved electrode, in which the hollow grid cells occupy ½ of the area of the whole curved electrode 19. When the curved electrode 19 is a ½ type curved electrode, it is convenient to calculate the resistivity.

Figure 6B:
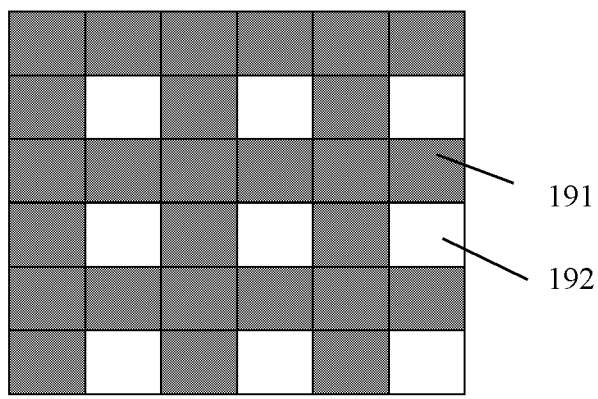
FIG. 6b illustrates a plane development diagram of another curved electrode provided in an embodiment of the present disclosure.

FIG. 6b illustrates a ¼ type curved electrode, in which the hollow grid cells occupy ¼ of the area of the whole curved electrode 19. When the curved electrode 19 is a ¼ type curved electrode, it is less likely to be deformed and more durable than the ½ type curved electrode.

In addition, the specific form of the curved electrode 19 is not limited to the above examples, and based on the actual need, a person skilled in the art can also select different grid-like curved electrodes 19 to be contacted with the core.

The displacement loop may comprise: a gas displacing water loop and a water displacing oil loop. In order to simplify the overall structure of the system, the gas displacing water loop and the water displacing oil loop may share the core holder 7. The gas displacing water loop may sequentially comprise a gas source 1, a pressure regulation mechanism, a first inlet valve 6, the core holder 7, a first outlet valve 9, and a gas-liquid separation metering device 11. The water displacing oil loop may sequentially comprise: a displacement pump 12, a water source, a second inlet valve 14, the core holder 7, a second outlet valve 15, and an oil-water separation metering device 16.

In the present disclosure, two opposite curved electrodes 19 are disposed outside the sleeve in the core holder 7, and corresponding curved electrode circuit is disposed to acquire a voltage value and a current value for the resistivity calculation; subsequently, the resistivity of the core is determined according to the current value, the voltage value, an arc length of the curved electrode 19, and a radius and a length of the core. Experiments prove that the resistivity measurement method provided by the present disclosure can acquire the resistivity of the plunger-type core 23 in a diameter direction, and it is particularly suitable for the anisotropic reservoir.

In relation to the prior art, the rock resistivity can be measured in the vertical direction under formation conditions for the plunger-type core, without changing the core preparation technology or method.

The resistivity measurement method provided by the present disclosure is to measure the rock resistivity in the vertical direction under formation conditions for the plunger-type core. The diameter of the plunger-type core may be 2.5 cm, and of course any other value. In the following specific embodiments, the description is mainly made by taking a plunger-type core with a diameter of 2.5 cm as an example, and the situation of any other diameter is similar to that of this diameter, which will be omitted herein.

The rock resistivity measurement method provided by the present disclosure may also be applied to measure the rock resistivity in the horizontal direction for the full-diameter core sample. Specifically, it is only necessary to match the sizes of the core holder 7 and the curved electrode 19 with the size of the full-diameter core sample.

Figure 7:
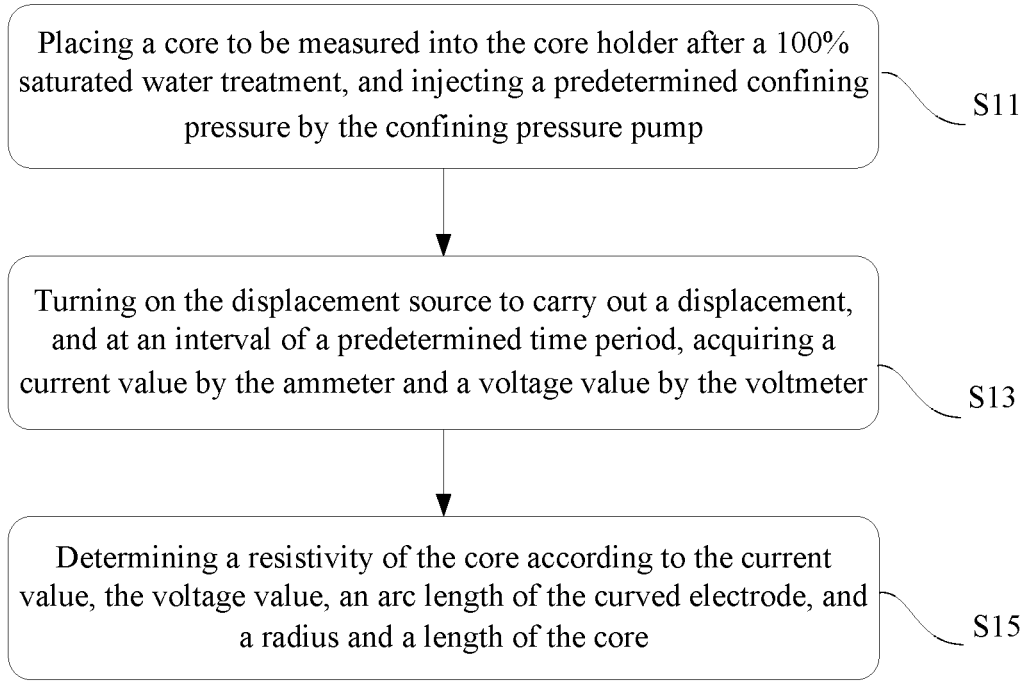
FIG. 7 illustrates a step flowchart of a resistivity measurement method provided in an embodiment of the present disclosure.

Referring to FIG. 7, based on the resistivity measurement system, the present disclosure further provides a resistivity measurement method so as to clearly and completely explain the resistivity measurement process. Specifically, the resistivity measurement method may comprise the following steps:

step S11: placing a core to be measured into the core holder 7 after a 100% saturated water treatment, and injecting a predetermined confining pressure by the confining pressure pump 8;

step S13: turning on the displacement source to carry out a displacement, and at an interval of a predetermined time period, acquiring a current value by the ammeter 18 and a voltage value by the voltmeter 25;

step S15: determining a resistivity of the core according to the current value, the voltage value, an arc length of the curved electrode 19, and a radius and a length of the core.

In this embodiment, the predetermined confining pressure may be a pressure greater than a displacement pressure by 2.5 MPa to 3 MPa. The displacement source may vary with the displacement experiment, for example, it may be a gas source 1, a water source, or any other type, and the detail is not limited herein.

In this embodiment, the predetermined time period is also not limited herein, wherein the predetermined time period may be a constant time interval, or an increasing time interval, or other signal acquisition interval. When the water saturation degree in the core tends to a fixed value and no longer changes, the experiment can be finished.

Determine a resistivity of the core according to the current value, the voltage value, an arc length of the curved electrode 19, and a radius and a length of the core specifically calculates according to a formula:

$$\rho(S_w) = \frac{h\Delta U}{J} \frac{K(k')}{K(k)}$$

wherein $$K(k) = \int_0^1 \frac{dx}{\sqrt{(1-x^2)(1-k^2x^2)}},$$

k=cos α, k'=sin α, $$\alpha = \frac{l}{2r},$$

ΔU denotes a voltage value acquired by the voltmeter 25, J denotes a current density, $$J = \frac{I}{A}, A = \frac{\pi rh}{2},$$

I denotes a current value read by the ammeter 18, r denotes a radius of the core, l denotes an arc length of the curved electrode 19, h denotes a length of the core, and $S_w$ denotes a water saturation degree of the core.

In addition, the method may further comprise: at the interval of the predetermined time period, acquiring an accumulated liquid amount through the separation recording device, and determining a saturation parameter of the core through the accumulated liquid amount and a pore volume of the core, wherein determining a saturation parameter of the core through the accumulated liquid amount and a pore volume of the core specifically calculates according to a formula:

$$S = \left(1 - \frac{V(t)}{V_p}\right) \times 100\%$$

Wherein V(t) denotes an accumulated liquid amount, which is measured in a displacement experiment, and $V_P$ denotes a saturation parameter of the core, which is a known value.

The common development processes in the oil and gas field development includes two main implementation scenarios: gas displacing liquid and liquid displacing liquid. In order to elaborate the present disclosure in detail, firstly the measurement method provided in the present disclosure will be described in detail in cases of gas displacing water and water displacing oil, respectively In a specific embodiment, the measurement system, which is configured to conduct a resistivity measurement experiment in a gas displacing water process and to conduct a resistivity measurement experiment in a water displacing oil process, may comprise: a gas source 1, a first pressure regulation valve 2, an intermediate container 3, a second pressure regulation valve 4, a pressure gauge 5, a first inlet valve 6, a core holder 7 with curved electrodes 19, a confining pressure pump 8, a first outlet valve 9, an exhaust valve 10, a gas-liquid separation metering device 11, a displacement pump 12, an intermediate container 13 with a piston, a second inlet valve 14, a second outlet valve 15, and an oil-water separation metering device 16.

In which, the gas source 1 is configured to provide gas required for an experiment. The gas may be an air source, a nitrogen source, or any other form of gas source, which is not limited herein.

The first pressure regulation valve 2, the intermediate container 3 and the second pressure regulation valve 4 are sequentially disposed between the gas source 1 and the core holder 7, and the first pressure regulation valve 2, the intermediate container 3 and the second pressure regulation valve 4 are cooperated to perform a pressure regulation for gas output from the gas source 1, so as to provide pressurized gas meeting a predetermined experimental requirement to the core holder 7.

The pressure gauge 5 is disposed between the second pressure regulation valve 4 and the core holder 7 for a real-time detection of a gas pressure supplied into the core holder 7. When the gas pressure does not meet the predetermined experimental requirement, a pressure regulation may be performed by adjusting the first pressure regulation valve 2 and the second pressure regulation valve 4, so that the gas pressure supplied into the core holder 7 meets the predetermined experimental requirement again.

The core holder 7 is provided with the curved electrodes 19. A curved electrode circuit is disposed between the two curved electrodes 19. Specifically, for the structures and compositions of the curved electrode 19 and the curved electrode circuit, please refer to the detailed description of the embodiment of the resistivity measurement system, and they will not be repeated herein.

In the gas displacing water process, the resistivity measurement process of the plunger-type core in its diameter direction is as follows:

S1: calculating a porosity of the core through a liquid saturation method or a helium method, and a pore volume of the core is known as $V_P$ (see GB/T 29172-2012 Practices for Core Analysis, P78-104). All the valves and pneumatic valves in the process are closed.

S2: placing the core into the core holder 7 with the curved surface electrodes 19 after the 100% saturated water treatment, so that the curved electrodes 19 fit perfectly with an axial surface of the core, recording an arc length in an axial direction of each curved electrode 19 fitting the axial surface of the core, calculating an included angle $2\alpha = l/r$ corresponding to the arc length, wherein r denotes a radius of the core, and injecting a pressure $P+\Delta P$ by the confining pressure pump 8 to ensure that the confining pressure of the core holder 7 is always greater than the displacement pressure, wherein $\Delta P$ is 2.5 to 3.0 MPa.

S3: turning on the gas source 1, opening the first pressure regulation valve 2 to introduce gas with a pressure P, opening the second pressure regulation valve 4 after the gas is stable in the intermediate container 3, and displacing the gas with the stable pressure P into the core holder 7; opening the first outlet valve 9 and the exhaust valve 10, reading accumulated liquid amounts at different time points through the gas-liquid separation metering device 11, recording the time t and the accumulated liquid amounts V(t) in a table, and calculating a water saturation degree of the core at each timing:

$$S_w = \left(1 - \frac{V(t)}{V_p}\right) \times 100\%.$$

S4: closing the switch 17, reading a current value I through the ammeter 18, reading a voltage value $\Delta U$ through the voltmeter 25, and calculating a conductivity of the core under the water saturation degree according to a formula:

$$\sigma(S_w) = \frac{J}{h\Delta U} \frac{K(k)}{K(k')}$$

Meanwhile, the resistivity is $$\rho(S_w) = \frac{h\Delta U}{J} \frac{K(k')}{K(k)},$$

wherein $$K(k) = \int_0^1 \frac{dx}{\sqrt{(1-x^2)(1-k^2 x^2)}},$$

$k = \cos \alpha$, $k' = \sin \alpha$, $$\alpha = \frac{l}{2r},$$

and $\Delta U$ denotes a voltage value acquired by the voltmeter 25, J denotes a current density, $$J = \frac{I}{A}, A = \frac{\pi r h}{2},$$

I denotes a current value read by the ammeter 18, r denotes a radius of the core, l denotes an arc length of the curved electrode 19, h denotes a length of the core, and $S_w$ denotes a water saturation degree of the core.

Through the above formula, the rock resistivity in the vertical direction under formation conditions can be acquired.

Figure 8A:
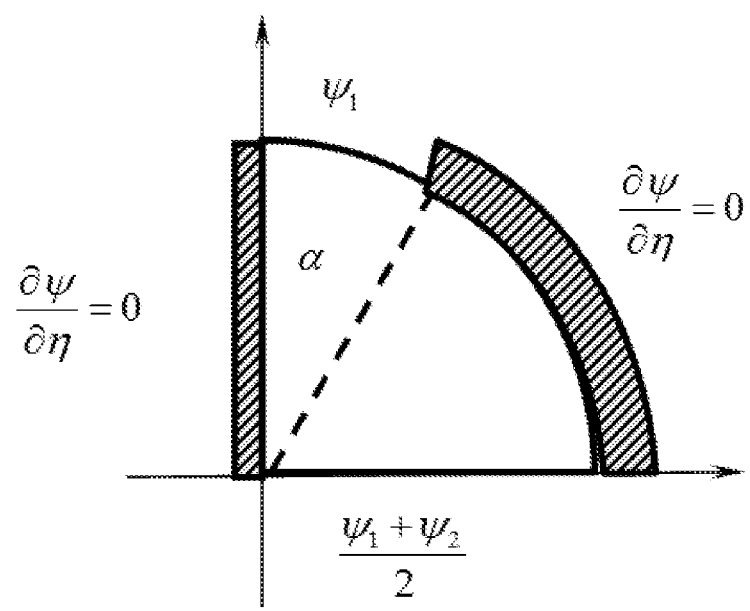
FIG. 8a illustrates a principle diagram for deriving a resistivity calculation formula in an embodiment of the present disclosure.
Figure 8B:
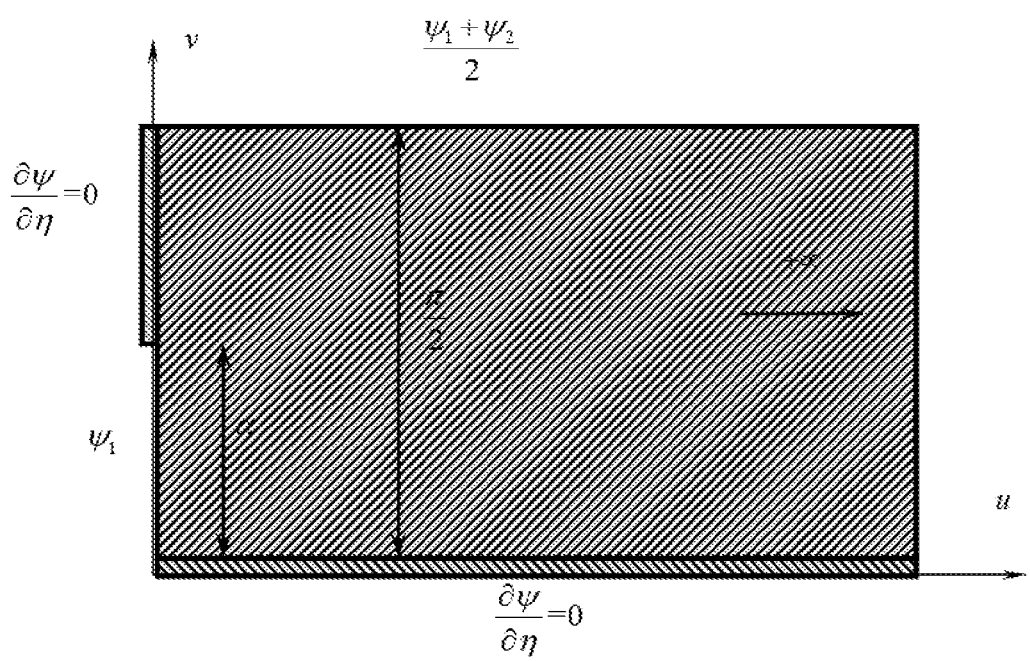
FIG. 8b illustrates a principle diagram for deriving a resistivity calculation formula in an embodiment of the present disclosure.
Figure 8C:
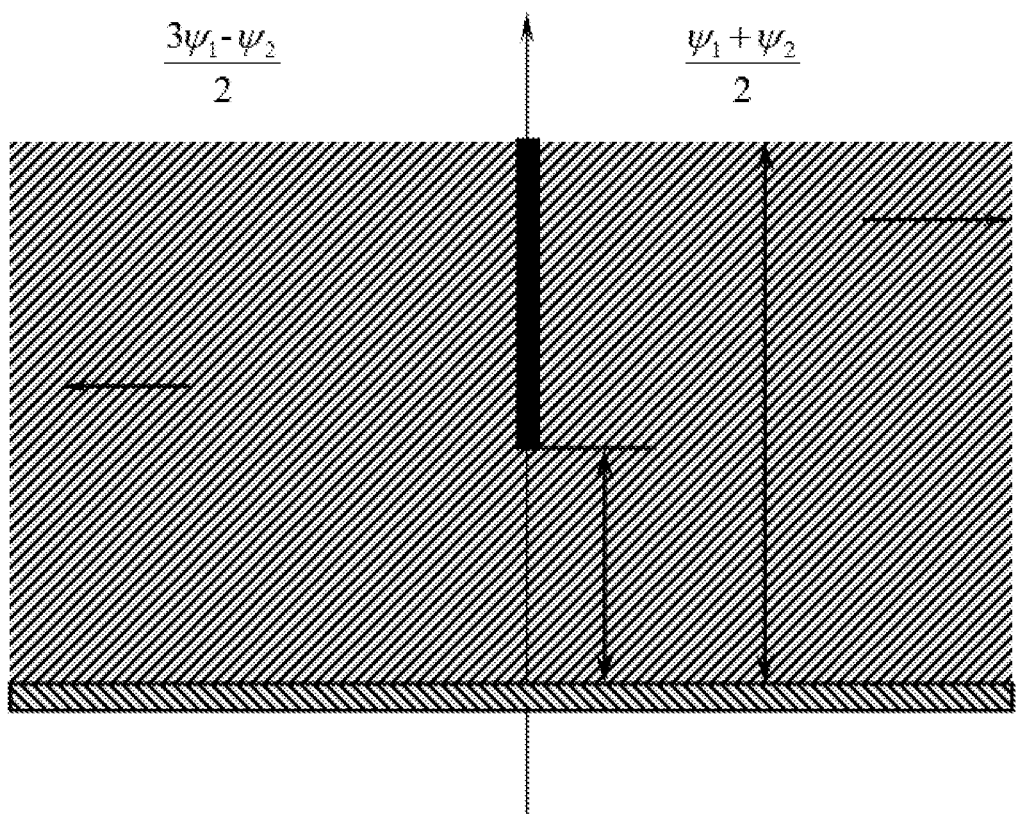
FIG. 8c illustrates a principle diagram for deriving a resistivity calculation formula in an embodiment of the present disclosure.

Referring to FIGS. 8a to 8c, specifically, the resistivity of the plunger-type core of the rock in the diameter direction is derived as follows:

Under a given temperature, there is a formula:

$$R = \frac{\rho L}{S},$$

wherein R denotes a resistance, ρ denotes a resistivity (Ω·m), L denotes a conductor length (m), and S denotes a cross-sectional area (m²).

Two cylindrical arc-shaped planar electrodes are placed at A-A' and B-B' of the cylindrical conductor, and a calculation formula of the resistivity between the two linear electrodes is derived.

According to the differential form of Ohm's law, for a uniform metal conductor:

$$U = IR (U = \varphi_a - \varphi_b) \quad (1)$$

Resistance $$R = \frac{\rho L}{S}, \quad (2)$$

ρ denotes a resistivity in a unit of Ω·m.

Conductivity $$G = \frac{1}{R} = \frac{1}{\rho} \cdot \frac{S}{L} = \sigma \frac{S}{L},$$

in a unit of $$\frac{1}{\Omega} = s \text{ (Siemens)}$$

(2) is substituted into (1) to obtain $$I = \frac{U}{R} = \frac{SU}{\rho L} \quad (3)$$

According to the defined current density $$J = \frac{\Delta I}{\Delta S},$$

(3) is converted into $$J = \frac{1}{\rho} \nabla U \quad (4)$$

Formula (4) is a differential form of Ohm's law, and it may also be expressed as J=σE, wherein the conductivity $$\sigma = \frac{1}{\rho},$$

and the electric field intensity E=∇U, denoted as $$j = \sigma \nabla U \quad \textcircled{1}$$

In an isolated system, the total charge quantity remains unchanged, which is called as the law of charge conservation. Taking any closed curve S in a conductor in which charge flows, the net quantity of charge flowing out through S in time dt should be equal to the decrease of the quantity of charge in S in the same time.

$$-dq = \iint_s \vec{\delta} \cdot d\vec{S} dt$$

$$\text{i.e., } \iint_s \vec{\delta} \cdot d\vec{S} = -\frac{dq}{dt}$$

This is the integral form of the current continuity equation. If the charge is distributed in the form of bulk charge, the above formula may be rewritten as:

$$\iint_s \vec{\delta} \cdot d\vec{S} = -\frac{d}{dt} \iiint_\tau \rho d\tau$$

The left side of the equal sign in the above formula is equal to a volume integral of a current density divergence, so it may be converted into:

$$\iiint_\tau \nabla \cdot j \, d\tau = -\iiint_\tau \frac{\partial \rho}{\partial t} d\tau$$

The integral of the above formula is carried out in a volume τ surrounded by the curved surface S; since the above formula holds for any closed curved surface, a differential form of the current continuity equation is obtained as:

$$\nabla \cdot j = -\frac{\partial \rho}{\partial t} \quad \textcircled{2}$$

For the current density, p=const, denoted as p=A®.

By combining ① and ③, it can be obtained: ρj=−Aσ∇U, which may be converted into $$\nabla \cdot j = 0 \quad \textcircled{4}$$

Here it is assumed that the resistivity remains independent of the spatial function, and in a steady state, equation ② becomes $$\nabla \cdot j = 0 \quad \textcircled{5}$$

By combining ④ and ⑤, it can be obtained:

$$\nabla^2 (A\sigma U) = 0 \quad \textcircled{10}$$

or ∇²ψ=0, wherein ψ=AσU

Formally speaking, ⑩ is a Laplace equation that satisfies Cauchy Riemann condition, and a conformal transformation may be employed for it.

(In consideration that FIG. 8*a* illustrates a ¼ circle, it sets that $z=re^{i\theta}$, and in the coordinates $(x, y) \to (r \cos \theta, r \sin \theta)$), $$e^{-u} = r$$
$$e^{-iv}ie^{-i\theta}, \text{ wherein } 0 < r < +\infty, 0 \le \theta \le \frac{\pi}{2}, \text{ i.e., } W = \ln i/z)$$

As illustrated in FIG. 8*b*, this plane is transformed into a seepage problem through a conformal transformation $W=\ln i/z$:

$$\Delta \psi = \frac{3\psi_1 - \psi_2}{2} - \frac{\psi_1 + \psi_2}{2} = \psi_1 - \psi_2$$

As illustrated in FIG. 8*c*, the above problem is solved by polygonal mapping (Schwartz-Christophel formula) on FIG. 8*b* to obtain:

$$J_1 \rho_1 = \frac{L}{G}(\psi_1 - \psi_2)$$

It is substituted to obtain $$J_1 \rho_1 = \frac{L}{G} A \sigma \Delta U$$

i.e., $J_1 \rho_1 = J_2 \rho_2 = J_2 A = \frac{L}{G} A \sigma \Delta U$ conductivity $$\sigma = \frac{J_2 G}{L \Delta U},$$

or resistivity $$\rho = \frac{L \Delta U}{J_2 G}$$

or represented as:
cross-sectional area $A=hK(k')$, and length $L=2K(k)$ $$\sigma = \frac{J_2}{h(U_1 - U_2)} \frac{K(k)}{K(k')},$$

wherein h is a length of the core;

In summary, under the water saturation degree $S_w$ of the core, the conductivity is:

$$\sigma(S_w) = \frac{J}{h \Delta U} \frac{K(k)}{K(k')}$$

Meanwhile, the resistivity is $$\rho(S_w) = \frac{h \Delta U}{J} \frac{K(k')}{K(k)}.$$

In the course of the experiment, after $S_w$, $\sigma(S_w)$ and $\rho(S_w)$ are recorded, the experiment is continued and $S_w$, $\sigma(S_w)$ and $\rho(S_w)$ are further recorded at a certain time interval until the water saturation degree approaches a stable value. The gas source 1, the first pressure regulation valve 2, the second pressure regulation valve 4, the first inlet valve 6, the first outlet valve 9 and the exhaust valve 10 are closed, the pressure of the confining pressure pump 8 is set as 0, the confining pressure pump 8 is stopped, the core is taken out from the core holder 7, and the experiment is finished.

In the water displacing oil process, the resistivity measurement method for the plunger-type core in its diameter direction is as follows:

S5: calculating a porosity of the core through a liquid saturation method or a helium method, and a pore volume of the core is known as $V_P$ (see GB/T 29172-2012 *Practices for Core Analysis*, P78-104). All the valves and pneumatic valves in the process are closed.

S6: placing the core into the core holder 7 with the curved surface electrodes 19 after the 100% saturated water treatment, so that the curved electrodes 19 fit perfectly with an axial surface of the core, recording an arc length in an axial direction of each curved electrode 19 fitting the axial surface of the core, calculating an included angle $$2\alpha = \frac{l}{r}$$

pressure $P+\Delta P$ by the confining pressure pump 8 to ensure that the confining pressure of the core holder 7 is always greater than the displacement pressure, wherein $\Delta P$ is 2.5 to 3.0 MPa.

S7: fully filling an upper side of a piston of the intermediate container 13 with water, starting the displacement pump 12 to pump liquid with a pressure P into the intermediate container 13, so that the water at the upper side of a piston is driven under the pressure P to open the second inlet valve 14 and the second outlet valve 15, reading the accumulated liquid amounts at different time points through the oil-water separation metering device 16, recording the time t and the accumulated liquid amounts V (t) in a table, and calculating an oil saturation degree of the core at each timing:

$$S_o = \left(1 - \frac{V_o(t)}{V_p}\right) \times 100\%.$$

S8: closing the switch 17, reading a current value I through the ammeter 18, reading a voltage value $\Delta U$ through the voltmeter 25, and calculating a conductivity of the core under the oil saturation degree according to a formula:

$$\sigma(S_o) = \frac{J}{h \Delta U} \frac{K(k)}{K(k')}$$

Meanwhile, the resistivity is:

$$\rho(S_o) = \frac{h\Delta U}{J}\frac{K(k')}{K(k)}.$$

For the derivation process of the conductivity or resistivity, please refer to the detailed description of the gas displacing water process, which will not be repeated herein.

In the course of the experiment, after $S_o$, $\sigma(S_o)$ and $\rho(S_o)$ are recorded, the experiment is continued and $S_o$, $\sigma(S_o)$ and $\rho(S_o)$ are further recorded at a certain time interval until the oil saturation degree approaches a stable value. The displacement pump 12, the second inlet valve 14 and the second outlet valve 15 are closed, the pressure of the confining pressure pump 8 is set as 0, the confining pressure pump 8 is stopped, the core is taken out from the core holder 7, and the experiment is finished.

In a specific application scenario, for example, the core samples are taken from the Triassic Xujiahe Formation in Sichuan Basin. It is known that the pore volume of the core is 1.30 ml, and the sample is a cylindrical core with a length of 3.836 cm and a diameter of 2.538 cm. In the specific measurement, the core with 100% saturated water is loaded into the core holder 7 with the curved electrodes 19 as required in S2. The centering angle 2α of the curved electrode 19 is $$\frac{\pi}{2}$$

(i.e., 90°), and the contact surface of the ¼ type curved electrode in FIG. 6b is adopted.

A confining pressure of 6 MPa is applied to the core holder 7 by the confining pressure pump 8, and the core is displaced with the nitrogen of 3 MPa, so as to observe the change of the liquid at the gas-liquid separation metering device 11. A direct current of 6.03V is applied to both ends of the electrode, and the change of ammeter 18 is recorded, so as to obtain the following data:

TABLE 1

| Test time | Liquid volume cm³ | Water saturation degree % | Current intensity mA | Current density A/m² | Sample resistance Ω | Temp. ° C. | Resistivity in diameter direction Ω · m |
|---|---|---|---|---|---|---|---|
| 9:00 | 0.0000 | 100.00 | 6.93 | 4.53 | 870.44 | 24.6 | 5.104 |
| 9:15 | 0.0849 | 93.45 | 4.73 | 3.10 | 1273.50 | 24.6 | 7.467 |
| 9:30 | 0.1516 | 88.31 | 4.30 | 2.81 | 1402.70 | 24.8 | 8.225 |
| 10:00 | 0.2472 | 80.94 | 4.06 | 2.66 | 1485.70 | 24.9 | 8.711 |
| 10:30 | 0.3392 | 73.85 | 3.36 | 2.20 | 1796.90 | 25.2 | 10.536 |
| 11:00 | 0.4630 | 64.30 | 3.26 | 2.14 | 1847.00 | 25.7 | 10.830 |
| 12:00 | 0.5576 | 57.01 | 2.67 | 1.75 | 2258.90 | 25.9 | 13.245 |
| 14:00 | 0.8125 | 37.36 | 0.88 | 0.58 | 6855.00 | 25.3 | 40.194 |

At the beginning, the liquid in the core has not yet entered the gas-liquid separation metering device 11. At this time, the water saturation degree of the core is 100%, and the reading of the ammeter 18 is 6.93 mA. According to $$J = \frac{I}{A} \text{ and } A = \frac{\pi rh}{2},$$

the current density at this time may be calculated to be 4.53 A/m². The temperature for performing the experiment is recorded, and the rock resistivity under the saturation degree may be calculated according to $$\rho(S_w) = \frac{h\Delta U}{J}\frac{K(k')}{K(k)},$$

wherein $$2\alpha = \frac{\pi}{2}, \alpha = \frac{\pi}{4},$$

k=cos α, k'=sin α, $$K(k') = K(k) = K\left(\frac{\sqrt{2}}{2}\right) \text{ and } \frac{K(k')}{K(k)} = 1.$$

Thus, when $$2\alpha = \frac{\pi}{2},$$

the rock resistivity may be simplified into $$\rho(S_w) = \frac{h\Delta U}{J}$$

under the water saturation degree $S_w$, and a result of 5.104 Ω·m may be obtained through the data substitution for calculation.

Similarly, 30 minutes later, the liquid entering the gas-liquid separation metering device 11 is recorded as 0.0849 ml, and the water saturation degree of the core at this time is calculated as 93.45%, while other data tests and calculations are the same as those in the previous step. At a time interval, these operations are repeated and recorded into Table 1.

Figure 9:
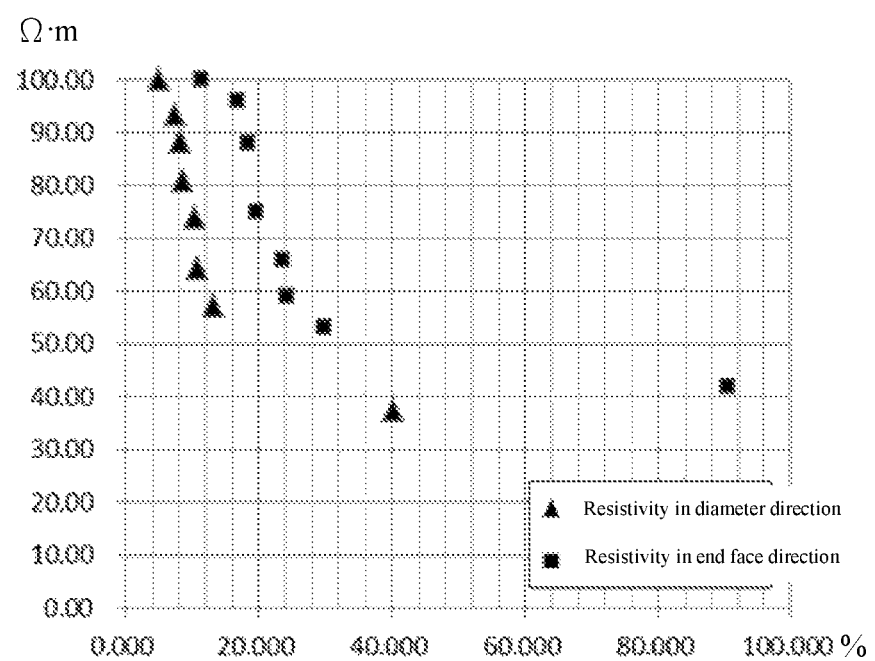
FIG. 9 illustrates a comparison diagram of resistivities in different directions of a same core provided in an embodiment of the present disclosure.

The experimental results are compared with the conventional resistivities measured in the end face direction, and the comparison results are illustrated in FIG. 9. In FIG. 9, the vertical coordinate represents the resistivity in ohms meters (106 ·m), and the horizontal coordinate represents the water saturation degree in %. It can be found that the resistivities measured in the diameter direction and the end face direction of the core sample are different.

Based on the core resistivity measurement system provided by the present disclosure, and through the core resistivity measurement method provided by the present disclosure, the measurement of the resistivity of the plunger-type core sample in the diameter direction is realized, and the acquired resistivity of the plunger-type core 23 in the diameter direction is particularly suitable for guiding the identification and development of anisotropic reservoirs.

Figure 10:
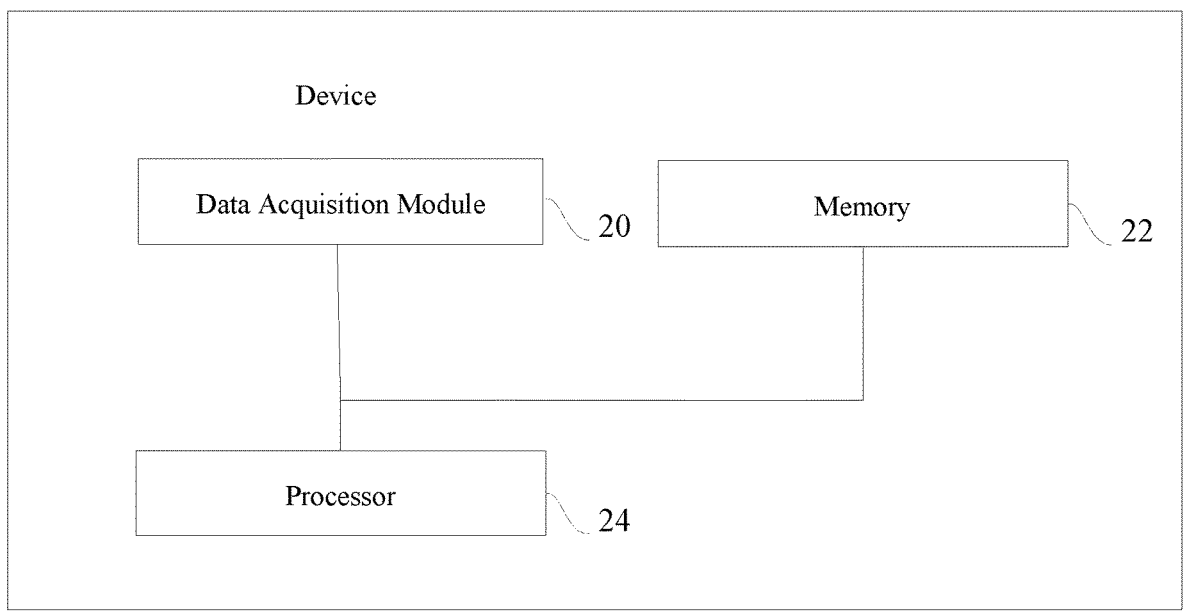
FIG. 10 illustrates a module diagram of a resistivity measurement device provided in an embodiment of the present disclosure.

Referring to FIG. 10, based on the above resistivity measurement method, the present disclosure further provides a resistivity measurement device, which may comprise:

a data acquisition module 20, a memory 22, and a processor 24, wherein the data acquisition module 20 is configured to acquire predetermined data, the memory 22 stores a predetermined correspondence relation for determining a resistivity according to the predetermined data acquired by the data acquisition module 20, and the processor 24 is capable of determining a resistivity of a core based on the predetermined data acquired by the data acquisition module 20 and the predetermined correspondence relation stored in the memory 22, wherein the predetermined data comprises arc lengths of curved electrodes 19 oppositely disposed on two sides of the core, voltage values at two ends of each curved electrode 19, current values flowing through the core, and a length of the core;

the predetermined correspondence relation is:

$$\rho(S_w) = \frac{h \Delta U}{J} \frac{K(k')}{K(k)}$$

wherein $$K(k) = \int_0^1 \frac{dx}{\sqrt{(1-x^2)(1-k^2 x^2)}},$$

k=cos α, k'=sin α, $$\alpha = \frac{l}{2r},$$

ΔU denotes a voltage value acquired by the voltmeter 25, J denotes a current density, $$J = \frac{I}{A}, A = \frac{\pi r h}{2},$$

I denotes a current value read by the ammeter 18, r denotes a radius of the core, l denotes an arc length of the curved electrode 19, h denotes a length of the core, $S_w$ denotes a water saturation degree of the core.

The resistivity measurement device is disposed in correspondence with the resistivity measurement method, and it can achieve the technical effects of the resistivity measurement method. The details are omitted herein.

In this embodiment, the data acquisition module 20 is configured to acquire the predetermined data, and electrically communicable with the processor 24 to transmit the acquired predetermined data to the processor 24.

In this embodiment, the memory 22 may include a physical device for storing information that is usually digitized and then stored in a medium using electronic, magnetic or optical methods. The memory 22 according to this embodiment may further include a device that stores information by means of electric energy, such as RAM and ROM; a device that stores information by means of magnetic energy, such as hard disk, floppy disk, magnetic tape, magnetic core memory, magnetic bubble memory and U disk; and a device that stores information optically, such as CD or DVD. Of course, there may be other forms of memories, such as a quantum memory, a graphene memory, etc.

In this embodiment, the processor 24 may be implemented in any suitable manner. For example, the processor 24 may take the form of, for example, a microprocessor or processor, a computer readable medium storing computer readable program codes (e.g., software or firmware) executable by the (micro)processor, a logic gate, a switch, an application specific integrated circuit (ASIC), a programmable logic controller, an embedded microcontroller, and the like.

Any numerical value quoted herein includes all of the lower values and the upper values that are increased by one unit from a lower limit value to an upper limit value, provided that there is an interval of at least two units between any lower value and any higher value. For example, if it is stated that the number of certain components or a value of a process variable (e.g., temperature, pressure, time, etc.) ranges from 1 to 90, preferably from 20 to 80, and more preferably from 30 to 70, the purpose is to explain that the Specification also explicitly lists the values such as 15 to 85, 22 to 68, 43 to 51, 30 to 32. For values less than 1, one unit is appropriately considered to be 0.0001, 0.001, 0.01 or 0.1. These are merely examples intended to be explicitly expressed, and it can be deemed that any possible combination of the values listed between a lowest value and a highest value is explicitly set forth in the Specification in a similar manner.

Unless otherwise specified, any range includes endpoints and all numerals between them. 'About' or 'approximately' used together with a range is suitable for both endpoints of the range. Thus, 'about 20 to 30' is intended to cover 'about 20 to about 30', including at least the indicated endpoints.

All the articles and references disclosed herein, including the patent applications and publications, are incorporated herein by reference for various purposes. Terms "substantially composed of . . . " for describing a combination should include the determined elements, constituents, components or steps as well as other elements, constituents, components or steps that substantively do not affect the essential novel features of the combination. The use of the term 'include' or 'comprise' to describe a combination of the elements, constituents, components or steps herein also contemplates embodiments substantially composed of such elements, constituents, components or steps. By using the term 'may' herein, it is intended to mean that any of the attributes described as 'may' is optional.

A plurality of elements, constituents, components or steps can be provided by a single integrated element, constituent, component or step. Alternatively, a single integrated element, constituent, component, or step may be divided into a plurality of separate elements, constituents, components or steps. The disclosure of 'a/an' or 'one' used to describe an element, constituent, component or step is not intended to exclude other elements, constituents, components or steps.

The above embodiments in this Specification are described in a progressive manner, and the same or similar parts of the embodiments can refer to each other, and each embodiment focuses on its differences from other embodiments.

Those described above are only a few embodiments of the present disclosure. Although the present disclosure reveals the embodiments as above, the description is only for the convenience of understanding the present disclosure and not intended to limit the present disclosure. A person skilled in the technical field of the present disclosure may make any modification and change to the forms and details of the embodiments without departing from the spirit and scope of the present disclosure, but the patent protection scope of the present disclosure should still be subject to the scope defined by the appended claims.

What is claimed is:

1. A resistivity measurement system, comprising:
at least one displacement loop, comprising a displacement source, an inlet valve, a core holder, an outlet valve and a separation recording device connected in sequence;
a confining pressure pump configured to apply a confining pressure to the core holder; wherein:
the core holder is configured to dispose a plunger-type core to be measured, a sleeve is disposed between the plunger-type core and the core holder, two opposite curved electrodes are disposed on the sleeve, inner surfaces of the two opposite curved electrodes are matched with an outer surface of the sleeve, and the two opposite curved electrodes are provided with openings for fluid circulation; and
a curved electrode circuit, comprising:
a power supply and a switch disposed between the two opposite curved electrodes, a voltmeter configured to measure a voltage between the two opposite curved electrodes, and an ammeter configured to measure a current flowing between the two opposite curved electrodes.

2. The resistivity measurement system according to claim 1, wherein the two opposite curved electrodes are in a form of a grid, comprising solid grid cells and hollow grid cells, a hollow grid cell being an opening for the fluid circulation, and a material of a solid grid cell being conductive metal.

3. The resistivity measurement system according to claim 2, wherein centering angles of the two opposite curved electrodes are greater than 0° and less than 180°.

4. The resistivity measurement system according to claim 3, wherein the centering angles of the two opposite curved electrodes are 90°.

5. The resistivity measurement system according to claim 1, wherein the displacement loop comprises a gas displacing water loop and a water displacing oil loop, wherein the gas displacing water loop and the water displacing oil loop share the core holder,
the gas displacing water loop sequentially comprising a gas source, a pressure regulation mechanism, a first inlet valve, the core holder, a first outlet valve, and a gas-liquid separation metering device; and
the water displacing oil loop sequentially comprising a displacement pump, a water source, a second inlet valve, the core holder, a second outlet valve, and an oil-water separation metering device.

6. A resistivity measurement method based on the resistivity measurement system according to claim 1, comprising:
placing a core to be measured into the core holder after a 100% saturated water treatment, and injecting a predetermined confining pressure by the confining pressure pump;
turning on the displacement source to carry out a displacement, and at an interval of a predetermined time period, acquiring a current value by the ammeter and a voltage value by the voltmeter; and
determining a resistivity of the core according to the current value, the voltage value, an arc length of the two opposite curved electrodes, a radius of the core, and a length of the core.

7. The resistivity measurement method according to claim 6, wherein determining the resistivity of the core according to the current value, the voltage value, the arc length of the two opposite curved electrodes, the radius of the core, and the length of the core is calculated according to a formula:

$$\rho(S_w) = \frac{h\Delta U}{J} \frac{K(k')}{K(k)}$$

wherein $$K(k) = \int_0^1 \frac{dx}{\sqrt{(1-x^2)(1-k^2x^2)}},$$

k=cos α, k'=sin α, $$\alpha = \frac{l}{2r}$$

ΔU denotes the voltage value acquired by the voltmeter, J denotes a current density, $$J = \frac{I}{A}, A = \frac{\pi r h}{2},$$

I denotes the current value read by the ammeter, r denotes the radius of the core, l denotes the arc length of the two opposite curved electrodes, h denotes the length of the core, $S_w$ denotes a water saturation degree of the core, x denotes a dimensionless coordinate in a radial direction of the core, and $d_x$ denotes a differential along the dimensionless coordinate.

8. The resistivity measurement method according to claim 7, further comprising: at the interval of the predetermined time period, acquiring an accumulated liquid amount through the separation recording device, and determining the water saturation degree of the core through the accumulated liquid amount and a pore volume of the core.

9. The resistivity measurement method according to claim 8, wherein determining the water saturation degree of the core through the accumulated liquid amount and the pore volume of the core specifically calculates according to a formula:

$$S_w = \left(1 - \frac{V(t)}{V_p}\right) \times 100\%$$

wherein V(t) denotes the accumulated liquid amount, which is measured in a displacement experiment, and $V_P$ denotes the pore volume of the core, which is a known value.

10. A resistivity measurement device, comprising: a data acquisition module, a memory and a processor, wherein the data acquisition module is configured to acquire predetermined data, the memory stores a predetermined correspondence relation for determining a resistivity according to the predetermined data acquired by the data acquisition module, and the processor is capable of determining a resistivity of a core based on the predetermined data acquired by the data acquisition module and the predetermined correspondence relation stored in the memory; wherein the predetermined data comprises arc lengths of curved electrodes oppositely disposed on two sides of the core, voltage values at two ends of each curved electrode, current values flowing through the core, and a length of the core;
the predetermined correspondence relation is:

$$\rho(S_w) = \frac{h\Delta U}{J} \frac{K(k')}{K(k)}$$

wherein $$K(k) = \int_0^1 \frac{dx}{\sqrt{(1-x^2)(1-k^2x^2)}},$$

k=cos α, k'=sin α, $$\alpha = \frac{l}{2r}$$

ΔU denotes a voltage value acquired by a voltmeter, J denotes a current density, $$J = \frac{I}{A}, A = \frac{\pi r h}{2},$$

I denotes a current value read by an ammeter, r denotes a radius of the core, l denotes the arc lengths of the curved electrodes, h denotes the length of the core, $S_w$ denotes a water saturation degree of the core, x denotes a dimensionless coordinate in a radial direction of the core, and $d_x$ denotes a differential along the dimensionless coordinate.

\* \* \* \* \*